United States Patent [19]

LaHaye

[11] 4,192,022

[45] Mar. 11, 1980

[54] ARTIFICIAL INTRAOCULAR LENS WITH IMPROVED STAVE

[75] Inventor: Peter G. LaHaye, Diamond Bar, Calif.

[73] Assignee: Iolab Corporation, San Dimas, Calif.

[21] Appl. No.: 901,127

[22] Filed: Apr. 28, 1978

[51] Int. Cl.² .............................. A61F 1/16; A61F 1/24
[52] U.S. Cl. ................................................................ 3/13
[58] Field of Search ............................................ 3/13, 1

[56] References Cited

U.S. PATENT DOCUMENTS

| 3,906,551 | 9/1975 | Otter ........................................... 3/13 |
| 3,996,626 | 12/1976 | Richards et al. ........................... 3/13 |
| 4,124,905 | 11/1978 | Clark ........................................... 3/13 |

OTHER PUBLICATIONS

Medical Workshop b.v.—Ordersheet Intraocular Lenses, Heresingel 28—Groningen—Holland.

Primary Examiner—Ronald L. Frinks
Attorney, Agent, or Firm—Jackson, Jones & Price

[57] ABSTRACT

An artificial intraocular lens designed for mounting within the anterior chamber of a patient's eye is disclosed. A substantially circularly shaped lens body which is refractive to light is provided with a pair of loops and a stave. The stave which is made of an elastic material such as polypropylene is fixedly mounted into an aperture in the lens body. The stave is provided with a keeper member on one side of a free end, the keeper member pointing away from an adjacent loop which is mounted to the same hemicircular segment of the lens as the stave. The opposite side of the stave provides a continuous substantially planar surface from the lens body to the free end of the stave. The loops are inserted behind the iris of the eye, and a surgical incision is made in the iris to permit the stave to be lead therethrough. The stave is capable of being bent until its free end traverses the loop, and as the bending force is released the keeper member engages the loop thereby fixedly positioning the lens in the eye. The opposite side of the free end is capable of assisting in the insertion of the keeper member by camming against the loop.

17 Claims, 6 Drawing Figures

ARTIFICIAL INTRAOCULAR LENS WITH IMPROVED STAVE

BACKGROUND OF THE INVENTION

1. Field of the Invention

The present invention relates to an improved artificial intraocular lens assembly used for the correction of aphakia and more particularly to an intraocular lens assembly having an improved stave and loop arrangement designed for mounting of the lens assembly in the anterior chamber of an eye.

2. Description of the Prior Art

The prior art is well aware of the use of artificial intraocular lens implants to produce stable retinal images with stable space localization. One of the common reasons for removing the natural lens of a patient is the condition of lenticular disease known as a cataract. The desirability of replacing the natural lens with an artificial lens to obviate the condition of aphakia is well known in the medical profession and has been in practice for a period of time. The prior art has developed a large number of lenses of different designs for surgical implantation in the anterior or posterior chamber of the eye.

Such prior art lenses are disclosed in the Richard U.S. Pat. No. 3,925,825; Fedorov U.S. Pat. No. 3,945,054; Krasnov U.S. Pat. No. 3,922,728; Richard U.S. Pat. No. 3,971,073, Richard U.S. Pat. No. 3,996,626; Fedorov U.S. Pat. No. 3,673,616; Potthast U.S. Pat. No. 3,913,148; Otter U.S. Pat. No. 3,906,551; Jensen U.S. Pat. No. 3,994,027; Flom U.S. Pat. No. 3,866,249, Krasnov U.S. Pat. No. 3,986,214 and in Flom U.S. Pat. No. 3,991,426. Additional disclosures concerning intraocular lens assemblies suitable for surgical implantation in the eye can be found in Scharf's German Pat. No. 959,314, Dannheim's German Printed Application No. 1,034,325, in the Proceedings of the Royal Society of Medicine Volume 58 Pages 729–731, Sept. 1965; and in the book "A Lens For All Seasons" by Gerald L. Tannant, published August 1976, pages 19–21, 41–29.

It will be readily understood that the surgical introduction of an artificial intraocular lens into the eye severely demands a medically acceptable and surgically and technologically feasible method of implanting the lens in the eye. The above described and other prior art devices have utilized various methods of fastening the lens in the eye. Generally speaking, anterior chamber lenses of the prior art are placed between the iris and the cornea, and are fastened therebetween by a number of loops or clips composed of a material having reasonable compatability with the eye tissue.

Otter U.S. Pat. No. 3,906,551 describes an anterior chamber intraocular lens which is provided with a pair of loops extending below the lens in a plane substantially parallel with the plane of a lower flat side of the lens. The loops of the Otter lens are surgically inserted below the iris and are held in a fixed position by a stave. One end of the stave is mounted into the lens while the other end is lead through a surgical incision in the iris and is designed to engage one of the loops and thereby hold the lens in a relatively fixed position in the eye.

As it will be readily appreciated by those skilled in the art an acceptable intraocular lens must satisfy, among others, the following requirements; it must be made from a material which is compatible with the eye tissue, and it must be sufficiently well fixed in position in the eye so that forces generated by movement of the person wearing the implanted lens should not dislodge the lens from its desired fixed position. Furthermore, the design of the intraocular lens must provide optimal conditions for the delicate procedure of surgically implanting the lens in the eye. Some of the disadvantages suffered by the prior art lenses lie in the fact that they do not satisfy one or more of the above requirements. More particularly some of the prior art devices have a relatively large surface in contact with the eye tissue thereby causing undue irritation, while other prior art lenses do not provide optimum conditions for the surgical implantation process.

As it can be readily appreciated from the above, the prior art is still seeking to provide an optimized artificial intraocular lens that can minimize or resolve the prior art problems and further simplify the surgical implantation of the lens with a minimal attendant possibility of damage of the patient.

SUMMARY OF THE INVENTION

It is an object of this invention to provide an anterior chamber intraocular lens which is designed to facilitate and simplify the surgical procedure required for its implantation in the eye.

It is another object of this invention to provide an anterior chamber intraocular lens which is well fixed in the eye and not subject to dislocation due to the forces generated by the movement of the patient wearing the implanted lens.

It is still another object of this invention to provide an anterior chamber intraocular lens which can be manufactured in a relatively simple and economical manner.

These and other objects and advantages are attained by the anterior chamber intraocular lens described in this invention. Into a lens body composed of a material refractive to light such as polymethylmethacrilate is mounted at least one loop and a stave. The loop is formed from a filament having two ends, the filament being composed of a material having good compatibility with the eye tissue such as e.g., polypropylene. Each end of the filament comprising the loop is affixed into an aperture which is located in the lens.

The loop substantially defines a plane lying below a flat surface of the lens which is in contact with the iris of an eye after surgical implantation.

An additional aperture having a longitudinal axis disposed perpendicularly to a longitudinal axis of the lens is provided in the lens. Yet another aperture having a longitudinal axis substantially parallel to the longitudinal axis of the lens, is disposed in the lens in such a manner that the two apertures partially intersect and form a T configuration, and that a filament comprising the stave can be inserted through the perpendicularly disposed aperture into the horizontally disposed aperture so that the filament extends horizontally from the lens.

The filament stave inserted through these apertures is made from an elastic material which is also compatible with the tissue of the eye such as for example a polypropylene material. A first end of the stave is provided with an enlarged head, the enlarged head being larger in diameter than the horizontally disposed aperture. Consequently after being inserted into the apertures the enlarged head of the stave prevents the stave from being pulled out in a lateral direction from the lens.

A section of the stave located in the horizontally disposed aperture is bent sufficiently so as to bring a periphery of the stave into intimate contact with the wall of the horizontally disposed aperture whereby the stave is fixed in relation to the lens. A second free end of the stave is provided with a protrusion on one side projecting away from the plane substantially defined by the loop, the protrusion defining a keeper member. Another side of the free end of the stave adjacent to the loop presents a contiguous planar camming surface.

As the lens is surgically implanted into the anterior chamber of the eye an incision is made in the soft spongy tissue of the iris and the free end of the stave is lead through the incision. The stave is then bent further to traverse the loop until the keeper member extending from the free end of the stave engages the loop and holds the lens in a fixed position. During the process of traversing the loop with the free end of the stave no resistance is encountered in view of the fact that only the smooth camming side of the stave comes into contact with the loop.

In the preferred embodiment of the present invention a second loop, disposed essentially in the same configuration as the first loop, is provided. The second loop is also inserted during the surgical procedure behind the iris wherein the lens is fixed in a position in the anterior chamber of the eye and held therein by the two loops, and the stave engaging one of the loops.

The objects and features of the present invention are set forth with particularity in the appended claims. The present invention may be best understood by reference to the following description, taken in connection with the accompanying drawings in which like numerals indicate like parts.

DESCRIPTION OF THE PREFERRED EMBODIMENT

The following specification taken in conjunction with the drawings sets forth the preferred embodiment of the present invention in such a manner that any person skilled in ophthamology lens design and ophthamological surgery can use the invention. The embodiment of the invention disclosed herein is the best mode contemplated by the inventor for carrying out his invention in a commercial environment, although it should be understood that various modifications can be accomplished within the parameters of the present invention.

Figure 1:
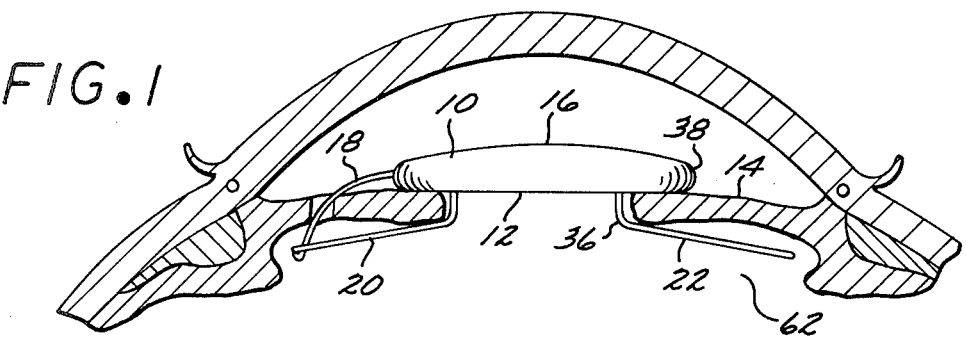
FIG. 1 is a schematic cross sectional representation of the anterior and posterior chambers of an eye with the lens of the present invention mounted therein.
Figure 2:
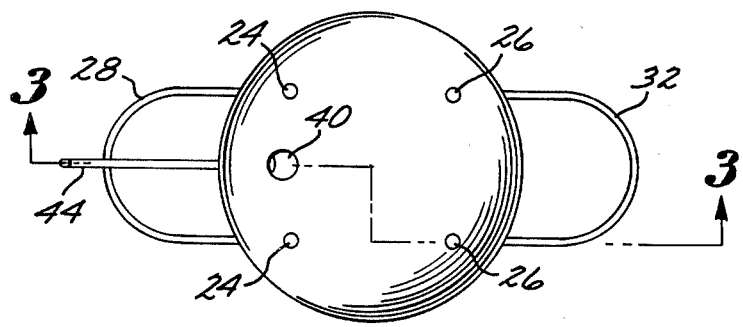
FIG. 2 is a top plan view of a preferred embodiment of the present invention.
Figure 3:
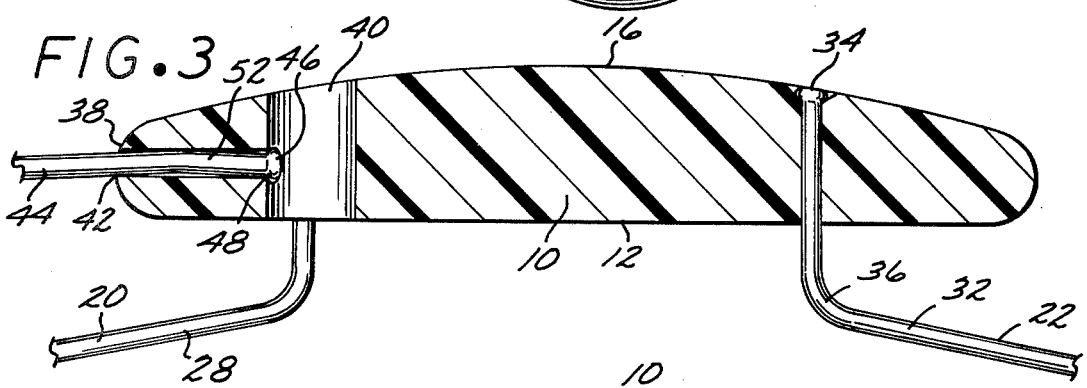
FIG. 3 is a cross sectional view of the preferred embodiment of the present invention, the cross section being taken at line 3—3 of FIG. 2.

Referring to FIGS. 1, 2 and 3 a substantially circular lens body made out of a material refractive to light such as for example polymethyl methacrylate is disclosed. The use of polymethyl methacrylate for the construction of the lens is particularly preferred in view of the fact that this material shows a desirably high compatibility with the eye tissue and therefore minimizes undersirable irritation. The lens body 10 has a substantially flat lower surface 12 which is designed to be partially in contact with the iris 14 of an eye, and a curved upper surface 16. The lens body 10 is provided with a stave 18 and a loop 20 located in a same hemicircular segment of the lens body 10 as the stave 18. Another hemicircular segment of the lens body 10 is provided with a second loop 22.

FIGS. 2 and 3 disclose in particularity the mounting of the loops 20 and 22 and of the stave 28 to the lens body 10. A pair of apertures 24 perpendicularly traversing the entire lens body 10 are provided in the lens body 10. Each of the apertures 24 are disposed equidistance from the center of the substantially circular lens body 10.

A second pair of apertures 26 perpendicularly traversing the entire lens body 10 is provided in another hemicircular segment of the lens body 10 in such a manner that the two pairs of apertures 24 and 26 comprise four corners of a square configuration with the center of the square being identical with the center of the substantially circular shaped lens body 10.

Two ends of a filament 28 comprising the first loop 20 are inserted into the first pair of apertures 24, the diameters of the apertures 24 being such that the filament 28 is held therein by friction. In order to further eliminate the possibility of accidental dislocation of the loop 20 from the apertures 24 and thereby from the lens body 10, each end of the filament 28 is provided with an enlarged head (not shown). As a convenient manufacturing technique the enlarged head (not shown) is placed on the filament 28 by some suitable method such as softening and deforming the material of the filament with localized heat, after the filament 28 has been inserted into the lens body 10. In the preferred embodiment of the present invention the exterior periphery of the enlarged head (not shown) of loop 20 lies flush with the curved upper surface 16 of the lens body 10.

A section of the filament 28 comprising the loop 20 extends below the flat lower surface 12 of the lens body 10 and is bent at an angle larger than 90°. Consequently the loop 20 itself which substantially defines a plane is located below and pointing away from the flat lower surface 12 of the lens body 10. An imaginary extension of the plane substantially defined by the loop 20 forms an acute angle with the flat lower surface 12 of the lens body 10. By way of example it is noted that in a preferred specific embodiment of the present invention the diameter of the filament 28 comprising loop 22 is approximately 0.17 mm and the angle formed between the imaginary extension of the plane defined by loop 20 and the flat lower surface 12 of the lens body 10 is approximately 10°.

A second filament 32 comprising a second loop 22 is affixed into the second pair of perpendicular apertures 26 in a manner substantially identical to the mounting of the first loop 20 into the first pair of apertures 24. The ends of the second filament 32 are also provided with enlarged heads 34 thereby preventing the accidental dislocation of the second loop 22 from the lens body 10. A section 36 of the second loop 26 extending below the flat lower surface 12 of the lens body 10 is bent in a manner substantially identical to the bending of the first loop 20.

The respective dimensions of the first 20 and second loops 22 are such that the loops 20 and 22 extend a substantial distance from the circular periphery 38 of the lens body 10.

By way of example, in a preferred embodiment of the present invention the diameter of the substantially circular shaped lens body 10 is 4.8 mm and the respective ends portions of loops 20 and 22 are at a distance of 8.0 mm from each other.

A fifth aperture 40 which also has a longitudinal axis perpendicular to the longitudinal axis of the lens body 10 and traverses the entire lens body 10, is provided in the lens body 10. A center of the fifth aperture 40 is located substantially on the imaginary line interconnecting the first pair of apertures 24 and is disposed at an equal distance from each of these apertures 24. The fifth aperture 40 is substantially larger in diameter than apertures 24 and 26, the purpose or providing this aperture with a larger diameter will be best understood from the description below.

A sixth aperture 42 having a longitudinal axis parallel with the longitudinal axis of the lens body 10 penetrates from the circular periphery 38 of lens body 10 to the fifth perpendicular aperture 40. The sixth aperture 42 is substantially smaller in diameter than the fifth aperture 40, and apertures 40 and 42 partially intersect to form a T configuration. A filament 44 comprising a stave 18 and having an enlarged head 46 on one end is inserted, with its second end 50 through perpendicular and horizontal apertures 40 and 42 until the enlarged head 46 is positioned at the junction 48 of apertures 40 and 42. The enlarged head 46, being larger in diameter than the horizontal aperture 42, prevents further movement of the stave 18 in the horizontal aperture 32. Accordingly after having been mounted into the lens body 10, the stave 18 extends from the circular periphery 38 of the lens body 10 in the direction of the longitudinal axis of the lens body 10.

Prior to mounting into the lens body 10, the stave 18 is provided with a bend 52 in an intermediate portion which is dimensioned to be located in the horizontal aperture 42. The bent portion 52 of the stave 18, after insertion into the horizontal aperture 42, is in intimate contact with the inner periphery of the aperture 42 and thereby creates sufficient friction so as to fixedly mount the stave 18 to the lens body 10.

Figure 4:
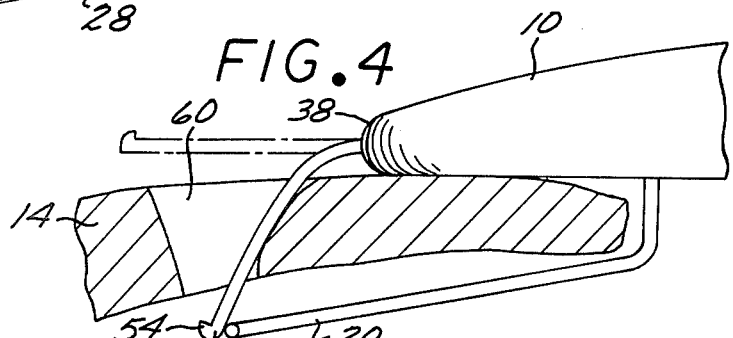
FIG 4 is a schematic partial side view of the preferred embodiment of the present invention in the process of being surgically implanted into the eye.
Figures 5, 6:
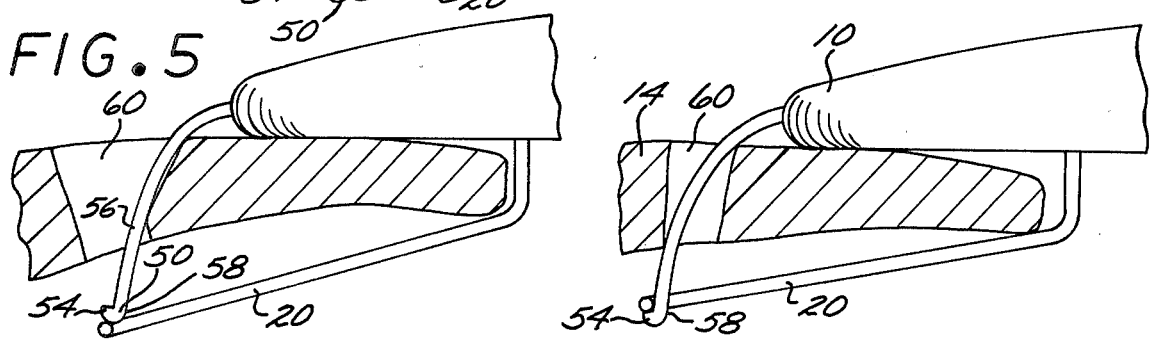
FIG. 5 is another schematic partial side view of the preferred embodiment of the present invention in the process of being surgically implanted into the eye.
FIG. 6 is a schematic partial side view of the preferred embodiment of the present invention after having been surgically implanted into the eye.

Referring particularly to FIGS. 4, 5 and 6, a protrusion at the second free end 50 of the stave 18 is shown to form a keeper member 54. It is an important feature of the present invention that the keeper member 54 provided on the stave 18 extends from only one side 56 of the free end of the stave 18 and in a direction opposite to the plane substantially defined by the first loop 20, while another side 58 of the free end of the stave 50 being adjacent to the loop is smooth and contiguous with the intermediate portion of the stave 18 to provide a camming surface.

The stave 18 as well as the loops 20 and 22 are manufactured from an elastic material such as polypropylene, and the respective dimensions of the stave 18 and of the first loop 20 are such that bending of the stave 18 towards the loop 20 allows the free end 50 of the stave 18 to traverse the loop 20, with only the smooth camming side 58 of the free end 50 coming into contact with the filament 28 comprising the loop 20. Due to the elasticity of the material comprising the stave 18 when a force bending the stave 18 below the plane defined by the loop 20 is released, a spring force is created desiring to reposition the stave in a configuration parallel with the longitudinal axis of the lens body 10. The keeper member 54 provided at the free end 50 of the stave 18 however, engages the loop 20 thereby affixing it into a permanently bent, hooked-up configuration.

The above described process of hooking the stave 18 in the loop 20 as it is done during the surgical procedure of implanting the lens in the anterior chamber of the eye is illustrated in FIGS. 4, 5 and 6.

It has been pointed out above that the surgical operation required for the implantation of intraocular lenses is extremely delicate. For this reason the fact that the keeper member 54 at the end of the stave 18 is pointing away from the plane defined by the loop 20 while the other side 58 of the free end 56 of the stave 18 is smooth, presents an advantage in that the smooth side 58 of the stave readily traverses the loop, for example with a sliding camming motion, while contacting the filament and thereby eliminates the need to bend the stave to the extent that would be necessary if the stave was to traverse the loop without coming into contact with the filament 28 comprising the loop 20.

In light of the above description it should be readily understood that the respective dimensions and relative angles of the various component parts of the lens system described here are designed to be optimal in providing a maximum possible degree of maneuverability during the surgical procedure. By way of an example, in a preferred embodiment of the present invention the diameter of the filament comprising a stave 18 is 0.15 mm and the stave 18 extends approximately 2.25 mm from the circular periphery 38 of the surgical lens body 10 while the loops 20 and 22 extend approximately 1.6 mm from the same.

Accordingly during the surgical procedure required for the implantation of the above described lens, an incision 60 is made in the soft spongy tissue of the iris 14. The loops 20 and 22 are inserted by a surgeon under the iris 14 into what is termed the posterior chamber of the eye 62, the stave 18 is then pulled through the incision 60 in the iris 14 and the free end 50 of the stave 18 is pushed through the first loop 20 positioned below the iris 14. In this process, due to the smooth camming surface provided on the free end 50 of the stave 18 which comes into contact with the loop 20, only minimal resistance is encountered. When the stave 18 is released by the surgeon, however, the keeper member 54 engages the loop 20 and thereby fixedly positions the entire lens in the patient's eye.

What has been described is an intraocular anterior chamber lens having an improved stave which simplifies the surgical procedure required for implantation of the lens. It will be apparent to those skilled in the art that various modifications of the present invention are possible and accordingly the scope of the present invention should be interpreted solely from the following claims.

What is claimed is:

1. An artificial anterior chamber intraocular lens having a longitudinal axis, the lens comprising:
   an optical zone lens body for refracting light;
   at least one loop fixedly mounted to the intraocular lens, a portion of the loop capable of being inserted behind an iris into a posterior chamber of an eye, and
   at least one stave having two ends, a first end being fixedly mounted to the intraocular lens, within a substantially horizontally disposed first aperture in the lens body, the stave having a substantially straight portion immediately adjacent to a second end, the second end bearing an enlarged head configured to project in a direction away from the loop and to define a keeper member on one side and a substantially continuous camming surface at the other side contiguous with an intermediate portion of the stave, the stave capable of being positioned so that the keeper member on the second end of the stave enters the loop and secures it wherein the lens body includes a substantially vertically disposed second aperture, the first and second apertures being disposed to communicate with one another, the second aperture permitting the stave to be fixedly mounted to the lens body.

2. The invention of claim 1 wherein the loop comprises a filament having two ends, each end being mounted respectively into an aperture in the lens which is substantially perpendicular to the longitudinal axis of the lens.

3. The invention of claim 2 wherein the loop comprises a section perpendicular to the longitudinal axis of the lens, a bend, and a second section, the second section being at an angle larger than 90° to the first section.

4. The invention of claim 3 wherein the stave is mounted into an aperture in the lens, the longitudinal axis of the aperture being substantially parallel to the longitudinal axis of the lens.

5. The invention of claim 4 wherein the lens is made of polymethyl methacrylate and the stave and the loop are made of polypropylene.

6. The invention of claim 2 wherein the stave is mounted into an aperture in the lens, the longitudinal axis of the aperture being substantially parallel to the longitudinal axis of the lens.

7. The invention of claim 1 further comprising a second loop, a portion of the second loop capable of being inserted behind the iris into the posterior chamber of the eye.

8. The invention of claim 7 wherein each loop comprises a filament having two ends, each end of each loop being mounted respectively into an aperture in the lens.

9. In an artificial anterior chamber intraocular lens including an optical zone lens body for refractint light, the lens having a substantially flat lower surface and a curved upper surface; at least one loop fixedly mounted to the intraocular lens, the loop substantially defining a plane being disposed below a plane defined by the flat lower surface of the lens, a portion of the loop capable of being inserted behind an iris into a posterior chamber of an eye, the improvement comprising:

a stave having first and second ends, the first end of the stave being fixedly mounted in an aperture in the lens body having an axis substantially parallel to the longitudinal axis of the lens so that the stave extends from the lens in a plane substantially parallel with the plane defined by the flat lower surface of the lens, the stave having a substantially straight intermediate portion immediately contiguous to the second end, the second end of the stave consisting of a solid protrusion which projects in a direction away from the loop to define a keeper member on one side and a substantially continuous camming surface at the other side contiguous with the intermediate portion of the stave, the stave capable of being positioned so that the keeper member on the second end of the stave enters the loop and secures it, a section of the stave mounted into the aperture in the lens body has a bent portion, the bent portion being in intimate contact with the inner periphery of the aperture whereby the stave is fixedly positioned in the aperture.

10. The improvement of claim 9 wherein the lens incorporates an additional aperture perpendicular to the longitudinal axis of the lens, the additional aperture and the aperture wherein the stave is mounted partially intersecting each other thereby forming a T configuration; and wherein the first end of the stave fixedly mounted in the lens incorporates a head, the head being larger than the diameter of the aperture wherein the stave is mounted, the head of the stave being positioned in a space created by the intersection of the apertures.

11. The improvement of claim 9 further comprising a second loop, a portion of the second loop capable of being inserted behind the iris into the posterior chamber of the eye.

12. The improvement of claim 11 wherein the lens is made of polymethyl methacrylate and the stave and the loops are made of polypropylene.

13. An artificial anterior chamber intraocular lens comprising:
a polymethyl methacrylate lens body including an optical zone for refracting light;
a first polypropylene loop fixedly mounted to the lens body, the first loop being substantially disposed below the lens body;
a flexible polypropylene stave mounted within a substantially horizontally disposed first aperture provided in the lens body, the stave extending constantly outward from the lens body and having an end located outside of the lens body, the stave having a proximate and a remote side relative to the first loop, a portion of the stave abutting the end being substantially straight, the end comprising a knob attached to the stave to provide a surface contiguous to the portion of the stave on the proximate side of the stave and to provide an angular surface relative to the remote side of the stave, the stave capable of being bent by a bending force to traverse the first loop with the camming surface sliding on the loop, the angular surface engaging the loop and keeping the stave in a bent position after the bending force is released wherein the lens body includes a substantially vertically disposed second aperture, the first and second apertures being disposed to communicate with one another, the second aperture comprising means for fixedly mounting the stave to the lens body.

14. The invention of claim 13 further comprising a second polypropylene loop substantially disposed below the lens body and adapted for positioning below an iris of a human eye.

15. An artificial anterior chamber intraocular lens having a longitudinal axis, the lens comprising:
an optical zone for refracting light;
at least one loop comprising a filament having two ends, each end being fixedly mounted respectively into an aperture in the lens which is substantially perpendicular to the longitudinal axis of the lens, a portion of the loop capable of being inserted behind an iris into a posterior chamber of an eye, and
at least one stave having two ends, a first end being fixedly mounted into an aperture in the lens, the longitudinal axis of the aperture being substantially parallel with the longitudinal axis of the lens, the lens incorporating an additional aperture perpendicular to the longitudinal axis of the lens, the additional aperture and the aperture wherein the stave is mounted partially intersecting each other thereby forming a T configuration, the first end of the stave fixedly mounted in the lens incorporating a head, the head being larger than the diameter of the aperture wherein the stave is mounted, the head of the stave being positioned in a space created by the intersection of the apertures; the stave having a protrusion substantially at a second end, the protrusion projecting in a direction away from the loop to define a keeper member on one side and a substantially continuous camming surface at the other side contiguous with the intermediate portion of the stave, the stave capable of being positioned so that the keeper member on the second end of the stave enters the loop and secures it.

16. The invention of claim 15 wherein the lens is made of polymethyl methacrylate and the stave and the loop are made of polypropylene.

17. The invention of claim 15 wherein a section of the stave mounted into the aperture in the lens has a bent portion, the bent portion being in intimate contact with the inner periphery of the aperture whereby the stave is fixedly positioned in the aperture.

* * * * *